United States Patent [19]

Cope et al.

[11] 4,042,634

[45] Aug. 16, 1977

[54] FLUOROCARBON SEPARATION PROCESS

[75] Inventors: Charles S. Cope; Maurice J. Couture, both of Parkersburg, W. Va.

[73] Assignee: E. I. Du Pont de Nemours and Company, Wilmington, Del.

[21] Appl. No.: 667,278

[22] Filed: Mar. 15, 1976

[51] Int. Cl.$^2$ ............................................ C07C 41/12
[52] U.S. Cl. ..................................... 210/616; 260/653
[58] Field of Search ................................. 260/616, 653

[56] References Cited

U.S. PATENT DOCUMENTS 3,635,926   1/1972   Gresham et al. ............... 260/87.5 A Primary Examiner—Howard T. Mars

[57] ABSTRACT

A process for removing the vapors of certain fluoro(alkyl vinyl ethers) from a mixture with the vapor of tetrafluoroethylene by contacting the mixture of vapors with a chilled aqueous liquid coolant solution that is substantially immiscible with the ethers. The process provides an advantageous method for recovering the fluoro(alkyl vinyl ether) monomer remaining in the polymerization kettle after it has been copolymerized with tetrafluoroethylene.

15 Claims, No Drawings

FLUOROCARBON SEPARATION PROCESS

FIELD OF THE INVENTION

This invention is directed to a process for separating fluoro(alkyl vinyl ethers) from tetrafluoroethylene, and more particularly to such a process carried out by direct-contact condensation.

BACKGROUND

Tetrafluoroethylene (TFE) and a fluorovinyl ether (FVE) are copolymerized (to make the copolymer TFE/FVE) in aqueous medium according to the procedure described in U.S. Pat. No. 3,635,926. In this procedure, at the end of the reaction the polymerization vessel contains.

1. a liquid phase comprising water, the copolymer TFE/FVE dispersed in the water, and the usual polymerization additives such as surfactant, buffer, and initiator, and initiator decomposition products. Some FVE monomer, and fluorocarbon polymerization solvent (if such is employed) are present in this phase in emulsified form or adsorbed on the polymer if the polymerization vessel is under pressure, 2. a denser liquid phase comprising unreacted FVE monomer and fluorocarbon polymerization solvent (if such is employed). Some TFE and chain transfer agent are present in this phase also, 3. a vapor phase comprising mostly unreacted TFE and some FVE, water vapor, gaseous chain transfer agent, and fluorocarbon polymerization solvent (if such is employed).

Several ways of recovering the copolymer and also recovering the TFE and FVE monomers have been tried or considered, but found impractical. These are:

a. withdrawing the water/copolymer phase (1) under autogenous pressure and leaving phases (2) and (3) in the vessel for the next polymerization. This has two disadvantages; first, part of the expensive FVE is in phase (1) and remains unrecovered, and second, some polymer remains in the polymerization vessel, causing coagulum formation and resulting in oversize polymer particles in the next polymerization.

b. withdrawing the denser bottom phase (2) under autogenous pressure. This method has the disadvantage of leaving too much FVE in the other two phases. Also phase (2) contains some entrained copolymer, leaving the FVE contaminated with copolymer.

c. withdrawing vapor phase (3), which will drop the pressure within the vessel to about the vapor pressure of liquid phase (2). Liquid phase (2) then bubbles up through aqueous phase (1) until phase (2) is vaporized. The disadvantages of this procedure are several. First, the vapor phase cannot be separated merely by cooling because the water vapor in it will freeze and eventually ice-up the equipment. Also complete separation is difficult because of the likelihood of fogging, with the recoverable components left entrained in the vapor vent stream. In addition, the FVE, TFE and any solvent present cannot be recovered by adsorption on activated charcoal because it catalyzes the polymerization of TFE.

Thus, a practical way of recovering unreacted monomers from this copolymerization process is desirable.

SUMMARY OF THE INVENTION

This invention removes the vapors of certain fluoro(alkyl vinyl ethers) and the vapors of certain fluorocarbon solvents (if such are present with the vinyl ether) from a mixture of them with the vapor of tetrafluoroethylene, by contacting the mixture of vapors with a chilled aqueous liquid coolant solution that is substantially immiscible with the ether (and the solvent, if solvent is present). The chilled aqueous liquid coolant solution liquefies the ether and the solvent, but is not chilled enough to liquefy the tetrafluoroethylene. The tetrafluoroethylene vapor is removed (by venting off), and may be cleansed of residual chain transfer agent and recycled for further use. The ether and the solvent (which are miscible in all proportions) are substantially immiscible with the chilled aqueous liquid coolant solution and are denser than the liquid solution. Thus, they form a liquid layer beneath the liquid coolant layer which can be separated from the liquid coolant by conventional two-layer liquid-separation procedures. Water vapor present in the vapor vent stream is simply absorbed by the liquid coolant solution.

More specifically, this invention is a process for separating vapors of tetrafluoroethylene and a fluoro(alkyl vinyl ether) of the formula $XCF_2(CF_2)_nO-CF=CF_2$ wherein X is F or H and n is an integer of 1–3 and optionally, a solvent vapor consisting essentially of a fluorocarbon solvent having a boiling point between about 0° and 75° C. at atmospheric pressure, and a freezing point such that a solution of it with the fluoro(alkyl vinyl ether) does not freeze at the lowest operating temperature of the process, which comprises:

1. contacting a vapor comprising tetrafluoroethylene, the fluoro(alkyl vinyl ether) and optionally, the fluorocarbon solvent, with a liquid coolant solution consisting essentially of water and a solute, said solute being present in an amount sufficient to a. impart a freezing point to the solution that is at least about 5° C. below the contacting temperature of the process (preferably at least about 10° C. below);

b. impart a density to the solution that is at least 0.05 g/cc above or below the density of the mixture of the fluoro(alkyl vinyl ether) and the solvent, if solvent is present;

c. impart a viscosity to the solution of below about 100 centipoises at the contacting temperature of the process;

said liquid coolant solution on one hand and the fluoro(alkyl vinyl ether), and, optionally the solvent, if solvent is present, on the other hand being substantially immiscible (i.e., the solubility of liquid coolant solution in the ether and the solvent, if present, is preferably less than 0.1% by weight at the operating temperature of the process), said contact being carried out at a temperature between about −40° and about 0° C., preferably between about −40° and about −20° C., 2. removing the liquid obtained from the contacting step, 3. separating the layer of ether and solvent, if solvent is present, from the layer of liquid coolant solution.

DESCRIPTION OF THE INVENTION

In its preferred aspect, the invention is employed after the polymerization of tetrafluoroethylene and the specified fluoro(alkyl vinyl ether) to removed the nonaqueous phases that are present in the polymerization vessel. The copolymerization of these monomers is described in U.S. Pat. No. 3,635,926. Separation of the monomers is conveniently accomplished by this invention by simply venting the vapors from the polymerization vessel into a zone containing the liquid coolant described herein above.

The first vapors vented from the pressurized polymerization vessel are composed predominantly of unreacted tetrafluoroethylene, but also contain minor amounts of the ether, the solvent (if employed) and water. As the venting of this vapor nears completion, the pressure inside the polymerization vessel is reduced until it is about equal to the vapor pressure of the dense bottom layer of liquid in the vessel. This layer then begins to vaporize and bubble up through the copolymer-rich layer and is vented off into the zone containing the liquid coolant solution.

Thus, as the vapors from the polymerization vessel vent into the zone containing the liquid coolant, the composition of vapors gradually changes until they are composed predominantly of unreacted ether monomers, with solvent (if used), and minor amounts of tetrafluoroethylene monomer and other entrained components of the polymer-rich aqueous layer.

After the bottom layer vaporizes, the copolymer-rich aqueous layer is removed and the copolymer recovered by conventional means, e.g., by coagulation, followed by decantation of liquid and by drying of the copolymer.

The function of the optional fluorocarbon solvent in the copolymerization of TFE and FVE monomers is described in U.S. Pat. No. 3,635,926. In selecting a solvent from among the several types enumerated in U.S. Pat. No. 3,635,926 which will also be suitable for the subsequent recovery of FVE, certain limitations are imposed by boiling-point and freezing-point considerations. The freezing point of the solvent must be below the lowest operating temperature of the recovery process (although some margin is allowed because the freezing point of the recovered solvent/FVE mixture will usually lie below that of the pure solvent). Preferably, the normal boiling point of the solvent should not lie above the temperature at which the copolymerization of TFE and FVE monomers is carried out, as described in U.S. Pat. No. 3,635,926; additionally, it should preferably be more than 20° C. above the operating temperature of the recovery process, to avoid excessive loss of solvent as uncondensed vapor in the recovery step.

Suitable solvents are listed below, together with their normal boiling points and freezing points.

| Formula | n.b.p., ° C | f.p., ° C. |
|---|---|---|
| $CCl_3F$ | 23.8 | −111. |
| $CCl_2FCClF_2$ | 47.6 | −35. |
| $CClF_2CClF_2$ | 3.6 | −94. |
| $CCl_2FCF_3$ | 3 | −56.6 |
| $CClF_2CClFCHF_2$ | 56.3 | −91.1 |
| $CClF_2CClFCClF_2$ | 73.7 | −72. |
| $CF_3CClFCCl_2F$ | 73.5 | −53. |
| $CF_3CClFCClF_2$ | 34.5 | −133. |
| $CClF_2F_2CClF_2$ | 35.8 | −125.4 |
| | 44.6 | −16.3 |

$$\begin{array}{c} CF_3 \\ | \\ F_2C-C-F \\ | \ | \\ F_2C-C-F \\ | \\ CF_3 \end{array} \text{ (\& isomers)}$$

Of these, $CCl_2FCClF_2$ is especially preferred. Mixtures of the above substances may be used, if desired.

The fluoro(alkyl vinyl ethers) used in the polymerization with TFE include perfluoro(ethyl vinyl ether), perfluoro(n-propyl vinyl ether) and perfluoro(n-butyl vinyl ether) and their analogs in which a terminal $—CF_3$ group in replaced by $—CF_2H$.

In carrying out the process of this invention, the vapors from the polymerization vessel are contacted with the liquid coolant described above. Contact can occur by bubbling the vapors into the liquid coolant, or, preferably, by introducing the vapors into a packed column while the liquid coolant circulates through it. Preferably the vapors are introduced near the bottom of the column while the liquid coolant cascades down from an entry point near the top of the column. The packing in the packed column is not critical and can be composed of any of the conventional types such as rings, saddles, spheres and the like. The column can also be a bubble-cap or sieve-tray column.

On contact between the vapors and the liquid coolant, the fluoro(alkyl vinyl ether) vapor and any solvent vapor present are condensed to liquid form while the other non-condensed vapor is vented from the contacting vessel.

The fluoro(alkyl vinyl ether) and solvent (if present) are normally miscible in all proportions. They are, however, substantially insoluble in the liquid coolant and are withdrawn as a separate liquid phase and reused directly in a subsequent polymerization.

One preferred liquid coolant is a solution of ethylene glycol in water. Preferably the ethylene glycol will be present in an amount of between about 50 and 85 precent by weight of the solution. This range of composition brackets the freezing-point minimum in the ethylene glycol—water system. Another preferred liquid coolant is a solution of calcium chloride in water in which the calcium chloride comprises between about 22 and 33 percent of the mixture by weight. The aqueous glycol solution can contain a small amount (e.g., between about 0.01 and 1.0 percent by weight of the solution) of a buffer such as borax to inhibit formation of acid in the solution when mild steel equipment is used.

The greater the temperature difference between the liquid coolant and the boiling points of the vapors that are to be contacted with the coolant, the better the degree of separation. Thus, the desired temperature of the coolant is between −40° and 0° C., preferably between −40° C. and −20° C. Because any water present in the vapors is condensed and becomes part of the aqueous portion of the coolant, no difficulties arising from icing are encountered in the process.

The solubility of the fluoro(alkyl vinyl ether) in the liquid coolant, and vice-versa, is virtually nil, so cross-contamination is negligible. There is a substantial difference in density (about 0.5 g/ml at −35° C.) between the two liquid phases, so separation of the fluoro(alkyl vinyl ether) phase from the aqueous liquid coolant phase (under quiescent conditions in a collection vessel) is rapid, and separation by simple decantation is practical. The separation is complete enough that the composition of the fluoro(alkyl vinyl ether) phase can be directly and conveniently measured by refractometry. The low solubility of the fluoro(alkyl vinyl ether) in the liquid coolant permits the latter to be continuously recirculated (with intermediate cooling), with very little fluoro(alkyl vinyl ether) and solvent, if present, held up as solute in the glycol phase.

An advantage of the direct-contact procedure used in this invention is that the process is conveniently operated at atmospheric pressure. Operation at higher pressures, e.g., 1–5 atmospheres or more, would, in principle, increase the levels of recovery achieved; however, the higher the pressure employed, the greater the amount of unrecovered polymerization ingredients left in the polymerizer when the pressures in the two vessels are balanced. The net result is a decrease in the overall degree of recovery when the pressure is raised. Thus although pressure is not critical, operation at atmospheric pressure is preferred.

A phenomenon frequently encountered while condensing vapors out of gas streams by passing the vapor-laden gases over chilled surfaces, as in a conventional shell-and-tube condenser, is the formation of a fog; i.e., a suspension of very finely divided droplets of the condensed vapor in the uncondensed portion of the gas. Fog formation is undesirable, as it can lead to high losses in the gas stream leaving the condenser, for the materials desired to be recovered. In the process of this invention, losses through fog formation are negligible.

The degree of recovery of the fluorocarbon solvent (when present) by the process of this invention is only moderate (at least in the case in which this solvent is $CCl_2FCClF_2$), since a significant portion (approximately half) remains emulsified with the aqueous dispersion layer and/or adsorbed on the dispersed polymer particles. Surprisingly, however, very little of the fluoro(alkyl vinyl ether) comonomer remains emulsified or absorbed, especially when the pressure in the polymerization vessel is reduced to atmospheric pressure. The only modest recovery of the solvent is acceptable, since its cost is relatively low. On the other hand, a high degree of recovery of the comonomer is essential, since its cost is high.

The degree of recovery of the fluorocarbon solvent can be improved by sparging the raw dispersion remaining in the polymerizer with nitrogen gas, and conducting the off-gas to the recovery system. However, this procedure is time-consuming and reduces the availability of the polymerization vessel for polymerization. The procedure also increases the risk of prematurely coagulating the raw dispersion in the vessel if the sparging is carried out too vigorously.

The packed column preferred for use herein can be operated over wide ranges of vapor and liquid coolant feed rates. Preferably, the weight rate of flow of the liquid coolant should be high relative to that of the vapor, so that the temperature of the exit vapors closely approaches that of the entering liquid coolant. Limitations on the allowable rates are set only by the well-known "loading" or "flooding" phenomena which occur in packed columns. In addition, the polymerization vessel must not be vented so rapidly that entrainment of raw dispersion into the recovery system occurs.

The separate addition of fluorocarbon solvent to the packed column (either as vapor or liquid) increases the potential degree of recovery of the fluoro(alkyl vinyl ether), since the added solvent lowers the partial pressure of the ether in the exit vapor. If added as liquid, the operating temperature must of course be above the freezing point of the pure solvent.

THE EXAMPLES

In the Examples which follow, vapors exiting from the pressurized polymerization vessel are conducted to a packed column recovery system where they enter near the bottom. Uncondensed gases exit the column near the top. The chilled aqueous liquid coolant enters the packed column near the top to provide counter-current flow to the vapor. Coolant containing condensed gas is drawn off the bottom of the column. The heavier condensed gas layer is separated from the coolant layer and the coolant recycled to the packed column.

The packed column employed comprises a 3-inch stainless steel pipe 60 inches long, which contains 45 inches of nominal ⅜-inch ceramic Berl saddle packing. A collection vessel below the packed column collects the liquid coolant and the ether layers. The vessel contains means for drawing off each layer. The liquid coolant is recirculated through a copper cooler and back to the top of the packed column. The entire system is enclosed and, when tested for leaks at 5.0 psig pressure of nitrogen gas over a 24-hour period, was found to be leakage free.

EXAMPLE 1

Tetrafluoroethylene (TFE) and perfluoro(n-propyl vinyl ether) (PPVE) were copolymerized to the copolymer TFE/PPVE in a polymerization vessel using $CCl_2FCClF_2$ as the fluorocarbon solvent, according to the general procedure described in U.S. Pat. No. 3,635,926.

During the course of this copolymerization, liquid coolant solution circulation was established in the packed column recovery system loop. A glycol solution containing 68 percent glycol by weight, 1 percent $Na_2B_4O_7$ by weight, and the balance water was employed as the liquid coolant solution. The level of glycol coolant solution in the 14-gallon capacity, stainless steel collection vessel underneath the packed column was maintained at about 60% full. The glycol coolant was circulated at the rate of 2250 pounds per hour per square foot of (empty) column cross-sectional area. Methylene chloride refrigerant, entering the cooler at $-40°$ C., was used to maintain the temperature of the glycol coolant stream entering the top of the packed column at about $-34°$ C.

When the desired level of solids content of copolymer (23 percent) had been achieved in the polymerization vessel, the TFE supply to the reactor was shut off and agitation stopped. Warm water was circulated to the jacket of the vessel to maintain approximately constant temperature during vent-down. The vapor from the 9.6-gallon polymerization vessel was vented off through a control valve into the packed column recovery system at the rate of about 170 standard cubic feet per hour per square foot of (empty) column cross-sectional area, giving a rate of pressure drop in the vessel of about 6 psi per minute. The piping connecting the polymerization vessel and the packed column had been steam-traced to prevent any condensation en route to the column. The glycol coolant circulation and the venting rates were maintained approximately constant until the pressure in the polymerization vessel had reached 75 psig. At this point, the rate of venting was reduced to 75 percent of its previous value (glycol coolant circulation rate remaining unchanged) in the interest of obtaining high overall recovery, since the bulk of the condensibles come over during the latter portion of the venting. Venting was continued until the pressure in the polymerization vessel reached 1 psig. The valve in the piping connecting the vessel and the packed column was then closed and nitrogen gas was admitted to the vapor space of the polymerization vessel until the pressure reached 75 psig. The contents of the vessel were agitated with a stirrer for 30 seconds at about 20 RPM. Agitation was stopped, and venting of the vessel was then resumed, at about two times the volumetric rate used initially. Venting was continued until the pressure in the polymerization vessel reached atmospheric. Glycol coolant circulation in the recovery system was then terminated. After ¾ hour had elapsed, the recovered condensibles were withdrawn through a valve located at the base of the collection vessel of the recovery system. The non-aqueous liquid was clear and colorless, and could readily be distinguished from the glycol coolant solution because of its much lower viscosity. The glycol coolant solution was slightly cloudy, but contained very little dissolved $CCl_2FCClF_2$ solvent and PPVE. In two experiments carried out under the same conditions, PPVE recoveries of 91 and 92.5 percent were achieved.

The recovered liquid in the PPVE layer was analyzed, after it had warmed to room temperature, by vapor-phase chromatography, with a confirmatory analysis by refractive-index measurement, and the data obtained are summarized in Table 1. In judging the performance of the recovery system, it was necessary to know how much PPVE and $CCl_2FCClF_2$ were actually present in the vapor stream when the vapor space of the polymerization vessel was vented down to atmospheric pressure. These amounts were measured in separate tests, in which the total amount of vapor was metered through a calibrated orifice, and the composition of the vapor was measured frequently during venting by means of vapor-phase chromatography. It was found, for polymerization runs identical to those used in the recovery tests described above, that about 146 grams of PPVE and 314 grams of $CCl_2FCClF_2$ were present in the vapor vent; the total amounts charged to the polymerizer were 548 grams and 625 grams, respectively, and, for the PPVE, about 392 grams of this charge became incorporated into the polymer product and hence were unavailable for venting. Although none of the $CCl_2FCClF_2$ solvent polymerizes, the fact that only about half the amount of it charged is present in the vented stream is believed to result from adsorption of the solvent by the colloidal particles of polymer in the aqueous phase. Fortunately, the amount of PPVE still adsorbed by the time the venting has been carried to 1 atmosphere is relatively small, so the bulk of the unpolymerized PPVE is available in the vapor stream vented into the packed column.

ample, the rapid "kick-off" of the polymerization was not delayed, and the reaction rate was not affected throughout the run. The product had essentially unchanged specific melt viscosity, molecular weight distribution, and combined PPVE content (as determined by infrared analysis) as those of products from runs made exclusively from "fresh" ingredients. The melt viscosity and molecular weight distribution measurements were carried out according to the procedures described in U.S. Pat. No. 3,635,926, except that the temperature of the melt indexer was maintained at 372°, rather than 380° C.

After a total of seven recovery runs, made under conditions similar to those reported above, there were no significant changes in the composition or pH of the glycol coolant solution. In separate tests, it was found that the amount of water brought over in the vapor vented from the polymerization reactor was typically only about 0.035 lb. under the conditions used. Knowing the quantity of aqueous glycol coolant solution present in the system, and from a knowledge of the freezing-point vs. composition relationship for aqueous glycol solutions, it was then possible to estimate that over 700 such recovery runs could be made before the pick-up of water would raise the freezing point of the aqueous glycol coolant solution to an operable level.

EXAMPLE 2

This example was carried out in a manner identical to that described in Example 1, except as described below. The glycol coolant solution was replaced with an aqueous solution containing 30 percent by weight of calcium chloride ($CaCl_2$) (technical grade). The aqueous $CaCl_2$ brine coolant was circulated at the rate of 2900 pounds per hour per square foot of (empty) column cross-sectional area. Methylene chloride refrigerant, entering the copper cooler at −40° C. to −45° C., was used to maintain the temperature of the calcium chloride brine coolant stream entering the top of the packed column at −34° C.

The vapor from the 9.6-gallon polymerization vessel was initially vented off through a control valve into the packed column recovery system at the rate of about 210 standard cubic feet per hour per square foot of (empty)

TABLE 1

| PPVE MATERIAL BALANCE | | | | | $CCl_2FCClF_2$ MATERIAL BALANCE | | | |
|---|---|---|---|---|---|---|---|---|
| (Weights in Grams) | | | | | (Weights in Grams) | | | |
| Charged to Polymerizer | Combined in Polymer | Recovered | Unaccounted For | Percent Recovery | Charged to Polymerizer | Recovered | Left in Dispersion | Percent Recovery From Polymerizer Vapor Vent |
| 548 | 392* | 146 | 10 | 93.5 | 625 | 314 | ~295** | ~95 |

*Obtained by infrared analysis of the polymer product. The infrared analysis had been calibrated by correlating the ratio of absorbances, at 10.07 and 4.25 microns wavelength for hot-pressed films 0.05 mm. thick, ofa series of polymers covering a range of combined PPVE contents with the difference in the amounts of PPVE charged to and vented from the polymerizer during synthesis.
** Obtained by vapor-phase chromatographic analysis of the raw dispersion recovered after polymerization, after adding a measured concentration of 2-pentanol as an "internal" standard.

The recovered liquids from two such experiments were then combined, without further treatment, to prepare the precharge for another polymerization run. By coincidence, the proportions of PPVE and $CCl_2FCClF_2$ in the recovered liquid were very nearly equal to those required in the precharge, so that very little adjustment by addition of fresh portions of either of these two ingredients was necessary.

In the polymerization using the precharge of recovered PPVE and $CCl_2FCClF_2$, the processing behavior was indistinguishable from that of runs made using the same proportions of entirely fresh ingredients. For excolumn cross-sectional area, and later reduced to about 70 percent of this value when the pressure in the reactor had dropped to about 75 psig. The temperature of the vapor leaving the packed column was about −5° C. Subsequent procedure followed that described in Example 1. The total time required for vent-down was about 1 hour. It is estimated that the total volume of vapors vented from the polymerization vessel was about 200 to 225 liters, as measured at 25° C. and 1 atmosphere absolute. The recovered liquid was analyzed by refractive-index measurement. Separation of the recovered liquid from the CaCl$_2$ coolant solution by decantation was found to be fully as easy as when glycol solution was employed.

The results obtained in several such experiments were quite reproducible, giving the apporoximate average values shown in Table 2.

As had been found when aqueous glycol was used as the coolant solution, the liquid recovered from the tests using calcium chloride brine as the coolant could be re-used directly in the PPVE/CCl$_2$FCClF$_2$ precharge for a subsequent polymerization (and recovery) run. No changes in processing or product performance were observed when recovered material was employed as part of the precharge.

TABLE 2

| PPVE MATERIAL BALANCE | | | | | CCL$_2$FCClF$_2$ MATERIAL BALANCE | | | |
|---|---|---|---|---|---|---|---|---|
| (Weights in Grams) | | | | | (Weights in Grams) | | | |
| jCharged to Polymerizer | Combined in Polymer | Recovered | Unaccounted For | Percent Recovery | Charged to Polymerizer | Recovered | Left in Dispersion | Percent Recovery From Polymerizer Vapor Vent |
| 535 | 356* | 156.5 | 22.5 | 87.5 | 625 | 326.4 | ~295** | ~99 |

*Obtained by infrared analysis of the polymer product. The infrared analysis had been calibrated by correlating the ratio of absorbances, at 10.07 and 4.25 microns wavelength for hot-pressed films 0.05 mm thick, of a series of polymers covering a range of combined PPVE contents with the difference in the amounts of PPVE charged to and vented from the polymerizer during synthesis.
Obtained by vapor-phase chromatographic analysis of the raw dispersion recovered after polymerization, after adding a measured concentration of 2-pentanol as an "internal" standard.

The embodiments of the invention in which an exclusive property or privilege is claimed are as follows:

1. A process for separating vapors of tetrafluoroethylene and a fluoro(alkyl vinyl ether) of the formula XCF$_2$(CF$_2$)$_n$O—CF=CF$_2$ wherein X is F or H and $n$ is an integer of 1–3, which comprises:
   1. contacting a vapor comprising tetrafluoroethylene, and the fluoro(alkyl vinyl ether) with a liquid coolant solution consisting essentially of water and a solute selected from the group consisting of a) ethylene glycol present in an amount between about 50 and 85 percent by weight of water and solute and b) Ca Cl$_2$ present in an amount between about 22 and 33 percent by weight of the water and solute; said liquid coolant solution on one hand and the fluoro(alkyl vinyl ether), on the other hand, being substantially immiscible; said contact being carried out at a temperature between about −40° C. and about 0° C.,
   2. removing the liquid obtained from the contacting step,
   3. separating the layer of ether from the layer of liquid coolant solution.
2. Process according to claim 1 wherein the liquid coolant is the mixture of ethylene glycol in water.
3. Process according to claim 1 wherein the liquid coolant is the mixture of CaCl$_2$ and water.
4. the process of claim 3 in which a solvent vapor consisting essentially of a fluorocarbon solvent having a boiling point between 0° C. and 75° C. at atmospheric pressure and a freezing point such that a solution of it with the fluoro(alkyl vinyl ether) does not freeze at the lowest operating temperature of the process, is present in the vapor described in step (1).
5. The process of claim 4 in which the solvent is CCl$_2$FCClF$_2$.
6. Process according to claim 4 wherein water is present in the vapors.
7. Process according to claim 6 wherein the fluoro(alkyl vinyl ether) is perfluoro(n-propyl vinyl ether), and wherein said contact is carried out at a temperature between about −40° C. and about −20° C.
8. Process according to claim 7 wherein the contact is made by passing the vapors into a packed column wetted by a flow of the coolant.
9. The process of claim 1 in which a solvent vapor consisting essentially of a fluorocarbon solvent having a boiling point between 0° C. and 75° C. at atmospheric pressure and a freezing point such that a solution of it with the fluoro(alkyl vinyl ether) does not freeze at the lowest operating temperature of the process, is present in the vapor described in step (1).
10. Process according to claim 9 wherein the vapors are vapors vented from a polymerization vessel wherein tetrafluoroethylene and a fluoro(alkyl vinyl ether) have been polymerized.
11. The process of claim 2 in which a solvent vapor consisting essentially of a fluorocarbon solvent having a boiling point between 0° C. and 75° C. at atmospheric pressure and a freezing point such that a solution of it with the fluoro(alkyl vinyl ether) does not freeze at the lowest operating temperature of the process, is present in the vapor described in step (1).
12. The process of claim 11 in which the solvent is CCl$_2$FCClF$_2$.
13. Process according to claim 11 wherein water is present in the vapors.
14. Process according to claim 11 wherein the fluoro(alkyl vinyl ether) is perfluoro(n-propyl vinyl ether), and wherein said contact is carried out at a temperature between about −40° C. and about −20° C.
15. Process according to claim 14 wherein the contact is made by passing the vapors into a packed column wetted by a flow of the coolant.

* * * * *